United States Patent
Wang et al.

(10) Patent No.: US 9,952,159 B2
(45) Date of Patent: *Apr. 24, 2018

(54) LASER INDUCED BREAKDOWN SPECTROSCOPY (LIBS) APPARATUS FOR ANALYZING BIOLOGICAL SAMPLES

(71) Applicants: Sean Xiaolu Wang, Wilmington, DE (US); Qun Li, Newark, DE (US)

(72) Inventors: Sean Xiaolu Wang, Wilmington, DE (US); Qun Li, Newark, DE (US)

(73) Assignee: BWT Property, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/235,170

(22) Filed: Aug. 12, 2016

(65) Prior Publication Data

US 2017/0045459 A1 Feb. 16, 2017

Related U.S. Application Data

(63) Continuation-in-part of application No. 14/845,980, filed on Sep. 4, 2015.

(60) Provisional application No. 62/205,045, filed on Aug. 14, 2015.

(51) Int. Cl.
  *G01J 3/30* (2006.01)
  *G01N 21/71* (2006.01)
  *G01J 3/10* (2006.01)
  *G01J 3/28* (2006.01)
  *G01J 3/443* (2006.01)
  *G01J 3/02* (2006.01)

(52) U.S. Cl.
  CPC .......... *G01N 21/718* (2013.01); *G01J 3/0208* (2013.01); *G01J 3/10* (2013.01); *G01J 3/28* (2013.01); *G01J 3/2803* (2013.01); *G01J 3/443* (2013.01); *G01N 2201/0612* (2013.01); *G01N 2201/129* (2013.01)

(58) Field of Classification Search
  CPC ................. G01N 21/71; G01N 21/718; G01N 2201/129; G01N 2201/0612; G01J 3/0208; G01J 3/10; G01J 3/28; G01J 3/2803; G01J 3/443
  See application file for complete search history.

(56) References Cited

U.S. PATENT DOCUMENTS

| 7,394,537 B1 | 7/2008 | Lindfors et al. |
| 7,999,928 B2 | 8/2011 | Beckstead et al. |
| 2004/0051867 A1* | 3/2004 | Brestel .................. G01J 3/2889 356/318 |

(Continued)

*Primary Examiner* — Jamil Ahmed

(57) ABSTRACT

This invention discloses a laser induced breakdown spectroscopy (LIBS) apparatus based on high repetition rate pulsed laser. The laser produces a train of laser pulses at a high repetition rate in the kHz (or even higher) range. When the laser beam hits the biological sample, it generates several thousands of micro-plasmas per second. Synchronized miniature CCD array optical spectrometer modules collect the LIBS signal from these micro-plasmas. By adjusting the integration time of the spectrometer to cover a plurality of periods of the laser pulse train, the spectrometer integrates the LIBS signal produced by this plurality of laser pulses. Hence the intensity of the obtained LIBS spectrum can be greatly improved to increase the signal-to-noise ratio (SNR) and lower the level of detection (LOD).

14 Claims, 5 Drawing Sheets

(56) References Cited

U.S. PATENT DOCUMENTS

| | | | |
|---|---|---|---|
| 2008/0151241 A1* | 6/2008 | Lindfors | G01N 21/718 356/318 |
| 2012/0033212 A1 | 2/2012 | Barefield, II | |
| 2014/0088876 A1* | 3/2014 | Shiley | G01V 13/00 702/8 |

* cited by examiner

LASER INDUCED BREAKDOWN SPECTROSCOPY (LIBS) APPARATUS FOR ANALYZING BIOLOGICAL SAMPLES

REFERENCE TO RELATED APPLICATION

This application claims inventions which were disclosed in Provisional Patent Application No. 62/205,045, filed Aug. 14, 2015, entitled "LASER INDUCED BREAKDOWN SPECTROSCOPY (LIBS) APPARATUS FOR ANALYZING BIOLOGICAL SAMPLES". The benefit under 35 USC § 119(e) of the above mentioned United States Provisional Application is hereby claimed, and the aforementioned application is hereby incorporated herein by reference.

This application is a continuation-in-part of U.S. application Ser. No. 14/845,980, entitled "LASER INDUCED BREAKDOWN SPECTROSCOPY (LIBS) APPARATUS BASED ON HIGH REPETITION RATE PULSED LASER", filed on Sep. 4, 2015, by Sean Xiaolu Wang and Qun Li. The subject matter of the aforementioned U.S. application is hereby incorporated herein by reference.

FIELD OF THE INVENTION

This invention generally relates to a laser induced breakdown spectroscopy (LIBS) apparatus, and more specifically to a laser induced breakdown spectroscopy (LIBS) apparatus for analyzing biological samples.

BACKGROUND

Trace minerals provide the essential nutrients that plant, animals, and humans need for metabolic functions such as growth and development, immunity and reproduction. Even moderate mineral deficiencies can produce severe adverse impact. It is reported that about one-third of the world human population suffers from mineral deficiencies. Thus there exists an urgent need for a field-deployable analytical instrument which can quickly detect mineral deficiencies in plant, animals, and humans.

The present invention discloses a laser induced breakdown spectroscopy (LIBS) apparatus for analyzing the content and concentration of trace elements in biological samples. Laser induced breakdown spectroscopy (LIBS) is a type of atomic emission spectroscopy which uses a highly energetic laser pulse as the excitation source. The laser pulse generates a high temperature micro-plasma on the surface of the sample. After this excitation, light that is characteristic of the elemental composition of the sample is emitted and analyzed within a spectrometer. In recent years, LIBS has become a very popular analytical method in view of some of its unique features such as applicability to any type of sample, practically no sample preparation, remote sensing capability, and speed of analysis.

SUMMARY OF THE INVENTION

The laser induced breakdown spectroscopy (LIBS) apparatus of the present invention is based on a high repetition rate pulsed laser. The laser produces a train of laser pulses at a high repetition rate in the kHz (or even higher) range. When the laser beam hits the biological sample, it generates several thousands of micro-plasmas per second. Synchronized miniature CCD array optical spectrometer modules collect the LIBS signal from these micro-plasmas. By adjusting the integration time of the spectrometer to cover a plurality of periods of the laser pulse train, the spectrometer integrates the LIBS signal produced by this plurality of laser pulses. Hence the intensity of the obtained LIBS spectrum can be greatly improved to increase the signal-to-noise ratio (SNR) and lower the level of detection (LOD).

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
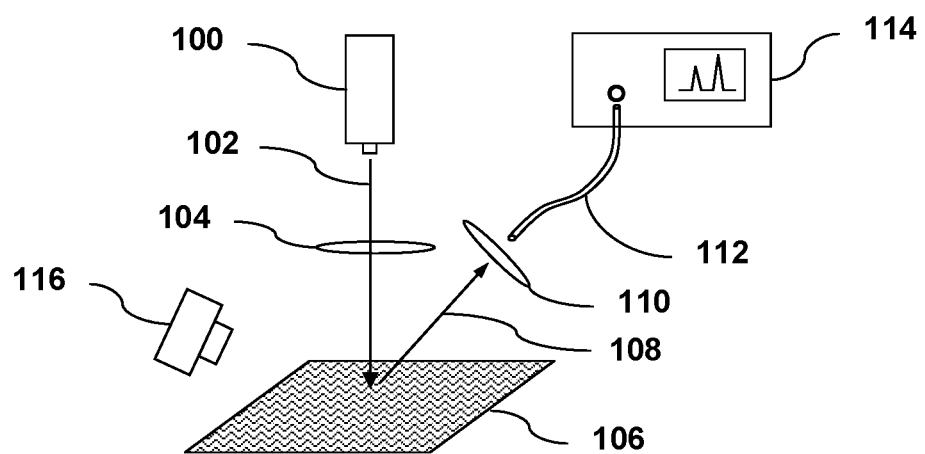
FIG. 1 illustrates an exemplary embodiment of the laser induced breakdown spectroscopy (LIBS) apparatus based on high repetition rate pulsed laser.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a laser induced breakdown spectroscopy (LIBS) apparatus for analyzing biological samples. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

An exemplary embodiment of the laser induced breakdown spectroscopy (LIBS) apparatus is shown in FIG. 1. The LIBS apparatus comprises a pulsed laser 100 as the excitation light source. The pulsed laser 100 is preferably a passively Q-switched diode-pumped solid-state (DPSS)

laser, which is capable of producing a train of laser pulses at a high repetition rate of >100 Hz, more preferably >1000 Hz (1 KHz). The pulse width of the laser is preferably less than 10 nanoseconds (ns), more preferably less than 1 nanosecond (ns). The laser beam 102 from the pulsed laser 100 is focused by an objective lens 104 onto a surface of the biological sample 106. The laser pulse produces a plasma emission, i.e. LIBS signal 108 at the surface of the biological sample 106, which is collected by a focusing lens 110 to be focused into a light guide 112, such as an optical fiber or fiber bundle. The light guide 112 then delivers the LIBS signal 108 into an optical spectrometer device 114 to obtain an optical spectrum of the LIBS signal 108. The LIBS spectrum is analyzed by a processor (not shown) to quantitatively evaluate the content and concentration of minerals in the biological sample 106. The processor may comprise a built-in chemometric model, which is constructed by calibrating the LIBS spectra of a set of standard biological samples with their mineral content and concentration, to facilitate the analysis.

The high repetition rate pulsed laser 100 of the present invention produces thousands of micro-plasmas per second from the biological sample 106. By adjusting the integration time of the spectrometer device 114 to cover a plurality of periods of the laser pulse train, the spectrometer device 114 can integrate the LIBS signal produced by a plurality of laser pulses. Hence the intensity of the obtained LIBS spectrum can be greatly improved to increase the signal-to-noise ratio (SNR) of the obtained LIBS spectrum. This unique feature of the high repetition rate laser based LIBS system allows it to measure trace elements with very low concentration, hence reducing the detection limit of the LIBS system. The increased signal intensity also lessens the sensitivity requirement for the optical spectrometer device 114. In addition, the energy of individual pulses in the laser pulse train can be reduced in comparison to conventional single shot or low repetition rate laser based LIBS system to obtain the same signal level. Hence the laser pulse is less invasive to the sample.

In a slight variation of the LIBS apparatus, the objective lens 104 and the focusing lens 110 may be replaced with other types of optical focusing elements, such as concave mirrors, to avoid chromatic aberration of the optical lenses. The objective lens 104 may be mounted on a vibration motor (not shown) or other types of vibration device, which causes the objective lens 104 to vibrate in a direction parallel with the sample surface. The vibration pattern can be either 1-dimentional (1-D) or 2-dimentional (2-D), which results in 1-dimentional (1-D) or 2-dimentional (2-D) lateral movement of the laser beam over the sample surface. Thus the laser beam is scanned over an area of the sample surface to excite LIBS signal from multiple measurement points. The optical spectrometer device 114 operates in a continuous mode to collect the LIBS signal from all these measurement points and obtains the corresponding LIBS spectra. Additionally, the vibration motor may cause the objective lens 104 to vibrate in a direction perpendicular to the sample surface. This vibration causes the laser beam to be focused at different depths on the sample surface. Thus the laser beam can produce plasma emission from at least a portion of the measurement points even though the sample surface is uneven. This laser beam movement, combined with the high repetition rate of the pulsed laser 100, allows one to collect LIBS spectra from hundreds to thousands of measurement points in just a few seconds. Since plenty of LIBS spectra are generated and collected over a short period of time, certain algorithm and criteria can be applied for sorting, selecting, and discarding certain groups and types of spectra for ensuring and improving the precision and accuracy of quantitative analysis of the elements.

Referring to FIG. 1, the position of the laser beam on the sample surface may be recorded by an imaging device 116, such as a camera. The position information is then correlated to the obtained LIBS spectrum of the corresponding measurement point to construct a two dimensional (2-D) spectral mapping of the sample surface.

Figure 2:
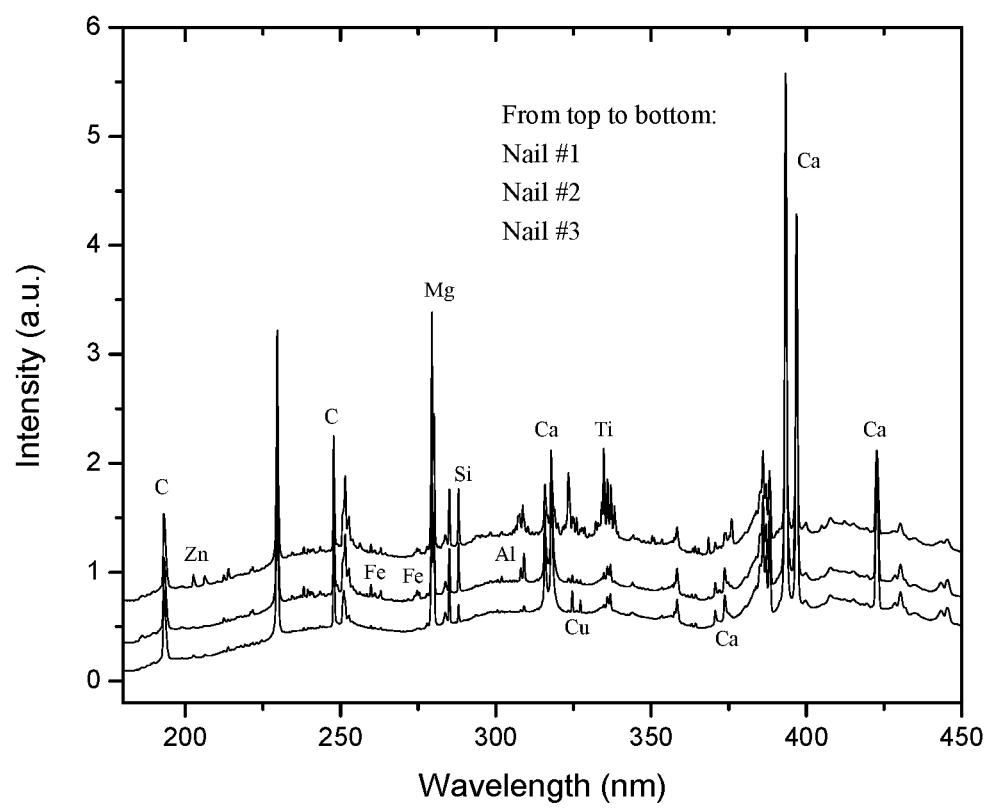
FIG. 2 shows the measured LIBS spectra of human nail samples from three individuals.
Figure 3:
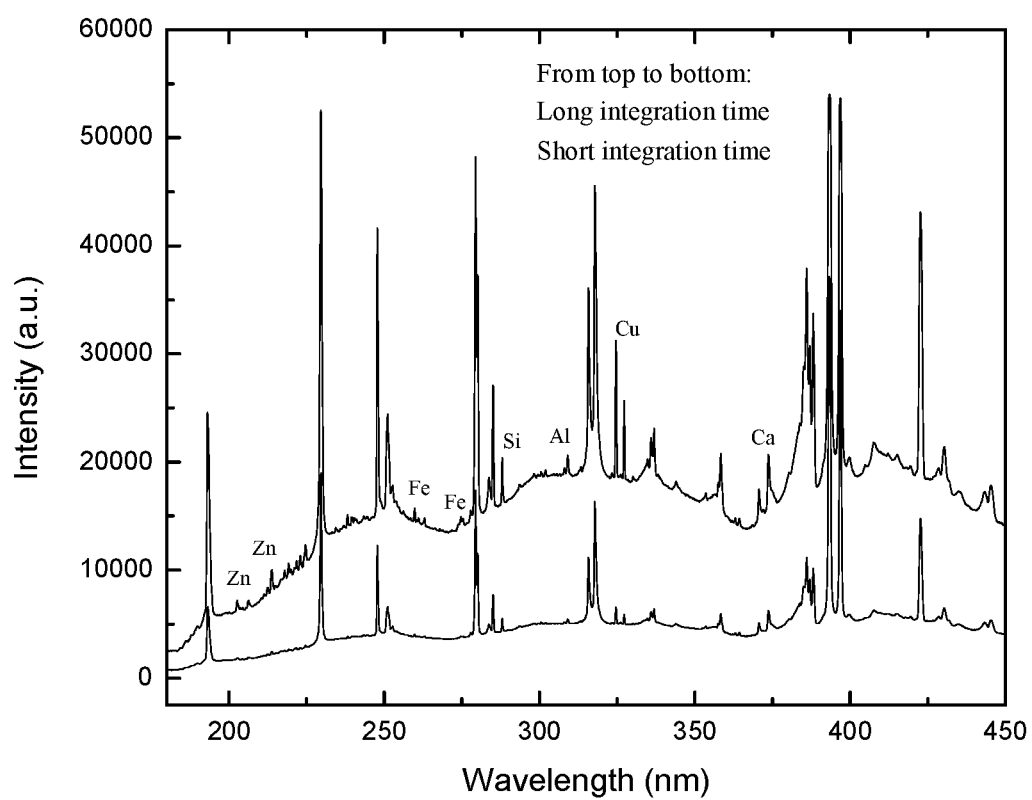
FIG. 3 shows the LIBS spectra of the same human nail sample measured at short and long integration time.

FIGS. 2-5 shows the LIBS spectra of a variety of biological samples measured by the high repetition rate LIBS apparatus as disclosed above. FIG. 2 shows the measured LIBS spectra of human nail samples from three individuals. The spectra clearly show the spectral lines for calcium (Ca), zinc (Zn), iron (Fe), silicon (Si), magnesium (Mg), copper (Cu), titanium (Ti), and aluminum (Al). The intensity of these spectral lines in reference to the carbon (C) lines may be used to estimate the concentration of the corresponding minerals. For example, it can be seen from the LIBS spectra that nail #1 has higher Zn content, while nail #3 has higher Cu content. The limit of detection (LOD) is on the order of a few ppm to a few tens of ppm. With the high repetition rate LIBS laser, the intensity of the collected LIBS spectra can be increased by simply increasing the integration time of the spectrometer device. This offers a 'magnified' version of the LIBS spectrum for trace element detection. Shown in FIG. 3 are the LIBS spectra of the same human nail sample measured at short (bottom) and long (top) integration time. The spectrum measured at long integration time clearly shows higher intensity for the trace elements such as Zn, Fe, Si, Al, and Cu, which reduces the LOD for these elements. LIBS measurement can be performed on a plurality of points along the length of the nail from the root to the tip and the positions of the measurement points can be recorded with the imaging device 116 of FIG. 1. The positions of the measurement points are associated with their corresponding LIBS spectra so that a histogram of the concentration of certain interested elements can be measured and recorded. Such a histogram may be used to correlate the element concentration with the food, medicine intake, environmental exposure, and/or the health status history of the subject. The LIBS measurement points can also be used as time markers so that the growth rate of the nails can be calculated together with the exact histogram of the interested elements.

Figure 4:
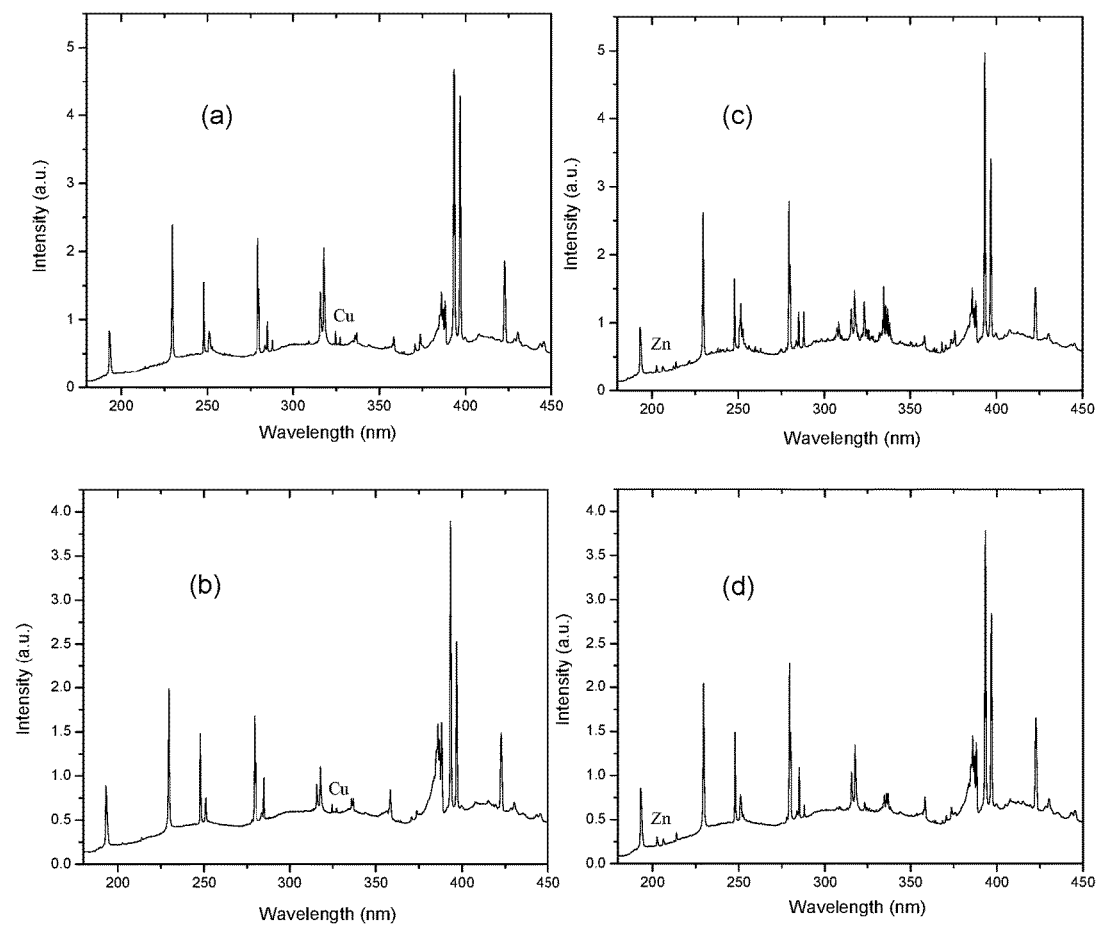
FIG. 4 shows a comparison of the LIBS spectra of hair and nail samples from two individuals.

FIG. 4 shows a comparison of the LIBS spectra of hair and nail samples from two individuals, where FIGS. 4 (*a*) and (*b*) are the spectra of the nail and hair sample from individual #1, and FIGS. 4 (*c*) and (*d*) are the spectra of the nail and hair sample from individual #2. It is interesting to note that the trace element concentration in nail and hair is consistent for the same individual. For example, individual #1 has higher Cu concentration in both her nail and hair, while individual #2 has higher Zn concentration in both her nail and hair. This verifies the capability of the LIBS apparatus for detecting mineral deficiency in human bodies.

Figure 5:
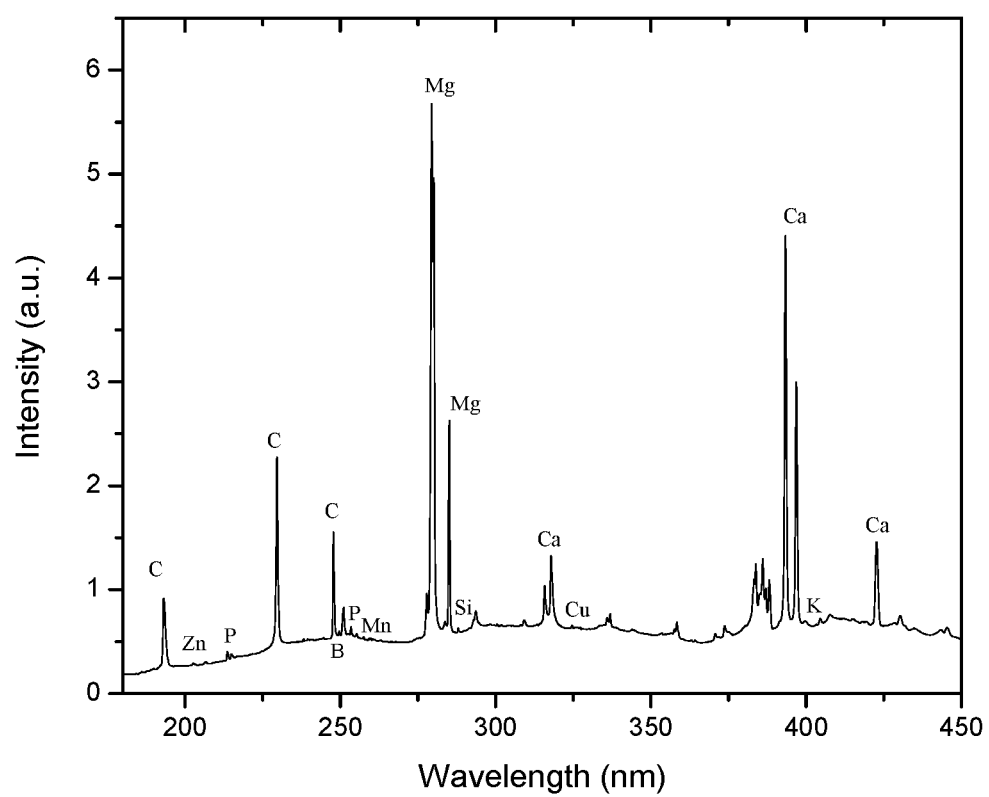
FIG. 5 shows the measured LIBS spectrum of a plant leaf sample.

Shown in FIG. 5 is the measured LIBS spectrum of a plant leaf sample. Here the leaf sample is first placed into an oven or microwave to remove the water content. The dehydrated leaf sample is then measured with the disclosed LIBS apparatus. The obtained LIBS spectrum clearly shows the spectral lines for both the macronutrients, such as K, Ca, Mg, P, and micronutrients, such as Zn, B, Mn, Cu. The intensity of these spectral lines in reference to the carbon (C) lines may be used to estimate the concentration of the corresponding minerals. This can help farmers to detect possible mineral deficiencies in their crops. By employing a laser with higher peak power and pulse energy, the LIBS apparatus can produce plasma emission from fresh leaf samples. Hence the step of dehydrating the sample can be skipped.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A laser induced breakdown spectroscopy (LIBS) apparatus for analyzing biological samples, the LIBS apparatus comprising:
    a high repetition rate pulsed laser light source configured to produce a laser beam in the form of a plurality of laser pluses at a high repetition rate;
    an optical focusing element configured to focus the laser beam onto a surface of the biological sample, wherein the plurality of laser pluses produce a plurality of plasma emissions from the surface of the biological sample;
    an optical spectrometer device operating in a continuous mode to measure an optical spectrum of the plurality of plasma emissions to obtain a LIBS spectrum; and
    a processor for analyzing the LIB S spectrum to evaluate a mineral content and concentration of the biological sample;
    wherein the optical spectrometer device is set to an integration time which covers a plurality of periods of the high repetition rate laser pulses.

2. The laser induced breakdown spectroscopy (LIBS) apparatus of claim 1, wherein the repetition rate of the laser pulse is greater than 100 Hz.

3. The laser induced breakdown spectroscopy (LIES) apparatus of claim 1, wherein the repetition rate of the laser pulse is greater than 1000 Hz.

4. The laser induced breakdown spectroscopy (LIES) apparatus of claim 1, wherein the laser pulses have a pulse width of less than 10 nanoseconds (ns).

5. The laser induced breakdown spectroscopy (LIES) apparatus of claim 1, wherein the laser pulses have a pulse width of less than 1 nanosecond (ns).

6. The laser induced breakdown spectroscopy (LIBS) apparatus of claim 1, wherein the pulsed laser light source is a passively Q-switched diode pumped solid state (DPSS) laser.

7. The laser induced breakdown spectroscopy (LIES) apparatus of claim 1, further comprising a vibration device configured to vibrate the optical focusing element to scan the laser beam over an area on the surface of the biological sample.

8. The laser induced breakdown spectroscopy (LIBS) apparatus of claim 7, wherein the vibration device vibrates the optical focusing element in a direction parallel with the surface of the biological sample.

9. The laser induced breakdown spectroscopy (LIBS) apparatus of claim 7, wherein the vibration device vibrates the optical focusing element in a direction perpendicular to the surface of the biological sample.

10. The laser induced breakdown spectroscopy (LIBS) apparatus of claim 1, further comprising an imaging device configured to record a position of the laser beam on the surface of the biological sample, wherein the position of the laser beam is associated with the corresponding LIBS spectrum.

11. The laser induced breakdown spectroscopy (LIBS) apparatus of claim 1, wherein the processor comprises a built-in chemometric model, said chemometric model is constructed by calibrating the LIBS spectra of a set of standard biological samples with their mineral contents and concentration.

12. A method for analyzing biological samples with laser induced breakdown spectroscopy (LIBS), the method comprising the steps of:
    producing a laser beam in the form of a plurality of laser pluses at a high repetition rate with a high repetition rate pulsed laser light source;
    focusing the laser beam onto a surface of the biological sample, wherein the plurality of laser pluses produce a plurality of plasma emissions from the surface of the biological sample;
    measuring an optical spectrum of the plurality of plasma emissions with an optical spectrometer device operating in a continuous mode to obtain a LIBS spectrum; and
    analyzing the LIBS spectrum to evaluate a mineral content and concentration of the biological sample;
    wherein the optical spectrometer device is set to an integration time which covers a plurality of periods of the high repetition rate laser pulses.

13. The method of claim 12, further comprising a step of scanning the laser beam over an area on the surface of the biological sample.

14. The method of claim 13, further comprising a step of recording a position of the laser beam on the surface of the biological sample with an imaging device and associating the position of the laser beam with the corresponding LIBS spectrum.

* * * * *